United States Patent [19]
Lee et al.

[11] Patent Number: 6,043,492
[45] Date of Patent: Mar. 28, 2000

[54] NON-INVASIVE BLOOD GLUCOSE METER

[75] Inventors: Shih-Ping Lee; Ran-Jin Lin; Hsiu-Hsiang Chen; Kuo-Kang Liu, all of Hsinchu, Taiwan

[73] Assignee: Industrial Technology Research Institute, Hsinchu, Taiwan

[21] Appl. No.: 08/958,338

[22] Filed: Oct. 27, 1997

[51] Int. Cl.[7] .......................... G01N 33/49; G01N 21/35
[52] U.S. Cl. .................................................. 250/339.12
[58] Field of Search .................................... 250/339.12

[56] References Cited

U.S. PATENT DOCUMENTS

| | | |
|---|---|---|
| 4,882,492 | 11/1989 | Schlager . |
| 5,077,476 | 12/1991 | Rosenthal . |
| 5,086,229 | 2/1992 | Rosenthal et al. . |
| 5,267,152 | 11/1993 | Yang et al. . |
| 5,321,265 | 6/1994 | Block . |
| 5,434,412 | 7/1995 | Sodickson et al. . |
| 5,460,177 | 10/1995 | Purdy et al. ............................ 600/436 |
| 5,550,373 | 8/1996 | Cole et al. ........................... 250/338.1 |

*Primary Examiner*—Constantine Hannaher
*Attorney, Agent, or Firm*—Stevens, Davis, Miller & Mosher, L.L.P.

[57] ABSTRACT

A non-invasive blood glucose meter includes a near-infrared energy analyzer which includes a light filter assembly of two Fabry-Perot interferometers and a photosensor. The near-infrared energy analyzer detects near-infrared energy absorbed by a human or animal body and generates spectra of such absorption so that the blood glucose content in the body may be analyzed. In order to provide stable energy absorption information of the blood, special designs are provided to stabilize the light source, to calibrate the spectrum and to obviate the noise from the heartbeats of the body. A single crystal silicon elastic power source is used to provide the driving power of the Fabry-Perot interferometer to avoid mechanical hysteresis.

10 Claims, 3 Drawing Sheets

NON-INVASIVE BLOOD GLUCOSE METER

FIELD OF THE INVENTION

The present invention relates to a non-invasive blood glucose meter, especially to a blood glucose meter comprising a near-infrared energy analyzer which comprises Fabry-Perot interferometers.

BACKGROUND OF THE INVENTION

The blood glucose meter is an important instrument to measure the glucose containing information in the blood of a human body or an animal body, especially for one suffering from diabetes. For diabetics, they have to measure the blood glucose content in their bodies from time to time so that the blood glucose content may be observed and controlled. A non-invasive blood glucose meter helps to avoid the painful blood removing procedure and is welcome by the doctors and the patents.

In the conventional art, a non-invasive glucose meter measures the blood glucose content by analyzing the near-infrared (near-IR) absorption spectra of the blood. However, due to the drifting in the discrete-type infrared sensor, as used in the conventional blood glucose meter, the near-IR absorption spectrum of the glucose can be deviated. In order to obtain stable blood glucose information, it is necessary to use a single-source-single-detector in the blood glucose meter.

In 1988, Schlager disclosed a non-dispersive differential two-beam energy absorption spectra measurement device (U.S. Pat. No. 4,882,492). In 1990 Rosenthal et al. disclosed a non-invasive measurement of blood glucose which uses a near-IR light emit device (LED) and a photo diode to non-invasively measure the blood glucose content in a human body by analyzing the near-IR transmission and absorption spectra of the blood (U.S. Pat. Nos. 5,086,229 and 5,077,476). In 1993, Yang disclosed a blood glucose meter which detects wave lengths from 1.3 to 1.8 $\mu$m. (U.S. Pat. No. 5,267,152). The above patents pertained to measurement of blood glucose contents by analyzing the absorption or scattering spectra of near-IR spots.

In 1992 and 1993, Myron Block disclosed a method to measure the blood glucose content. In this invention, a near-IR filter is used. (U.S. Pat. Nos. 5,321,265 and 5,434,412). In 1995 Myron Block further disclosed an assembly of multiple Michilson interferometers. Under the architecture of this patent, a wide-band light source is used.

In order to obtain multi-band energy absorption spectra, a conventional blood glucose meter comprises an assembly of multiple laser diodes and photodiodes. Decay in illumination and drifting in light color, however, are noted in the laser diodes under strong illumination. This harms the correctness of the measurement. Moreover, as discrete components are used in the conventional art, different magnitudes shall be applied in different bands of the absorption spectrum. This makes calibration complicated. Although Myron Block disclosed a feasible proposal, the original color sensing components used in his invention are always not stable which made it difficult to be commercialized.

It is thus a need in the industry to provide a novel non-invasive blood glucose meter which is compact, can measure the energy absorption of blood from the extrusive portions of human body and can avoid the drawbacks of the conventional discrete components while a uniformed magnitude can be applied to all bands in the absorption spectrum.

OBJECTIVES OF THE INVENTION

The purpose of this invention is to provide a compact non-invasive blood glucose meter that provides blood glucose information through analyzing the near-IR absorption spectrum of blood, measured at the extrusive portions of the human body.

Another purpose of this invention is to provide a novel non-invasive blood glucose which is able to provide continuous spectrum so that the aging of the optical components may not affect measurements thereof.

Another purpose of this invention is to provide an integrated near-IR absorption measurement instrument of blood so that continuous near-IR absorption spectra may be generated.

SUMMARY OF THE INVENTION

The non-invasive blood glucose meter of this invention comprises a near-infrared energy analyzer which comprises a light filter and suited photo diodes. The light filter of this invention comprises an assembly of two Fabry-Perot interferometers. The blood glucose meter is an integrated device prepared under microsystem technology (MST). Stable and continuous energy absorption spectra of blood may be generated so that a uniform magnitude may be applied to all the related bands and the aging of the components such as the light source and the photo diode will not affect the measurements.

In order to obtain stable energy absorption information of the blood, special designs are provided to the stabilize the light source, to calibrate the spectra and to obviate the affection from heartbeats. A silicon monolithic elastic power source is used to drive said Fabry-Perot interferometer so that mechanical hysteresis may be avoided.

The above an other purposes and advantages of this invention may be clearly understood from the detailed description of the invention by referring to the following drawings.

DETAILED DESCRIPTION OF THE INVENTION

The present invention presented a non-invasive blood glucose meter comprising Fabry-Perot interferometers prepared under the micro-system technology.

Figure 1:
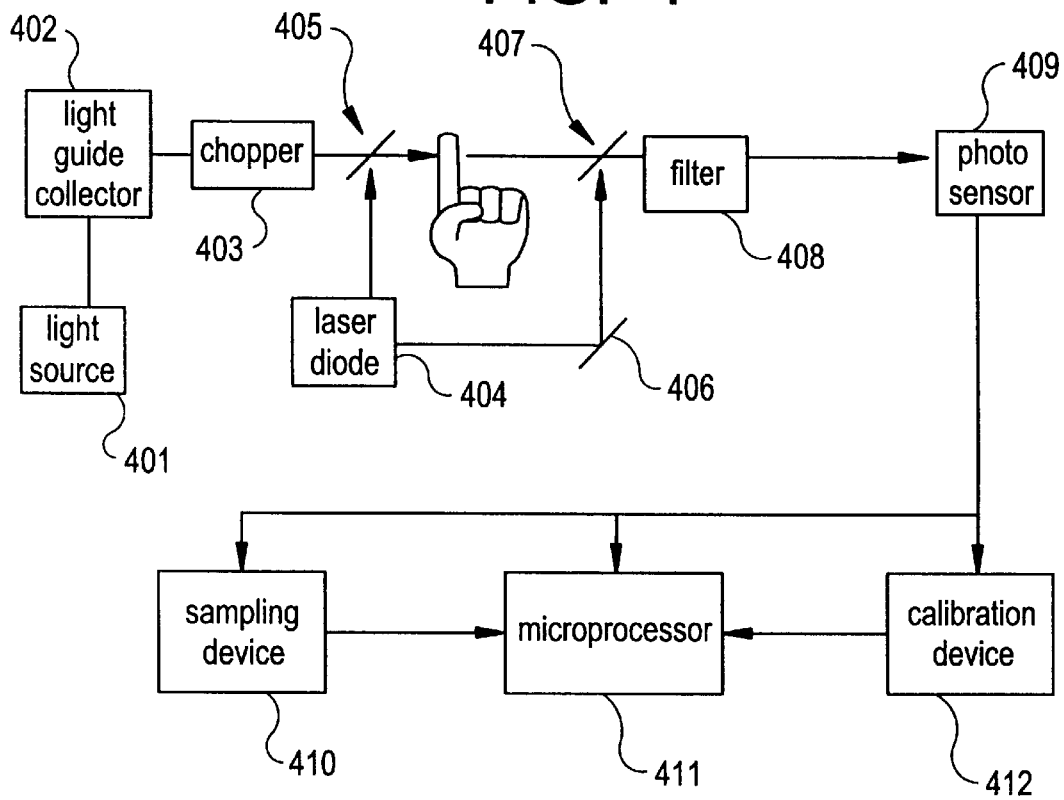
FIG. 1 illustrates the system schematics of the non-invasive blood glucose meter of this invention.

FIG. 1 illustrates the system schematics of the non-invasive blood glucose meter of this invention. As shown in the figure, the non-invasive blood glucose of this invention comprises: a light filter 408 to function as wave length selector, a photo diode 409 to function as photosensor, an incandescence light source 401 to provide incident light and a light guide-collector 402.

The light source 401 provides incident light which is projected to the extrusive portions of a human body or an animal body, such as a finger or a earlobe. The energy of the light is absorbed by the blood contained in such body and the residual is filtered by the light filter 408 and measured by the photo sensor 409. The information contained in the residual light represents the glucose content in the blood which is then analyzed by a microprocessor 411. A database of general blood glucose absorption vectors and a database of the variations in the blood glucose content of particular diabetics are stored in the microprocessor 411. The information as measured by the photo sensor may be calibrated and compared with the databases so that the blood glucose conditions of particular diabetics may be monitored. The scattering of the incident light inside the measured body may be used as a second light source so that the blood content in the subepidermal portions may also be measured.

Although it is not intended to limit the scope of this invention, it is found that Fabry-Perot interferometers may be used in the blood glucose meter to provide a continuous energy absorption spectrum. A Fabry-Perot interferometer is able to provide stable gains within an applicable range of wave lengths. This and other characteristics made it possible to provide a continuous spectrum analyzer using one single light source, with applicable photo diodes are used. The Fabry-Perot interferometer applicable in this invention uses single crystal silicon to provide mechanical power so to avoid the mechanical hysteresis.

The incandescence light source 401 of this invention includes a tungsten halogen light which may be controlled by a stability controller (not shown) so that the surface temperature of the filament may be maintained at about 3000 K with a variation of several tenths of one degree K. This may provide stability of the spectra within the scope of, for example, 0.8–1.7 μm. The stability of the spectra may be achieved by a feed-back control loop which measures the surface temperature of the filament and uses the temperature to continuously and simultaneously adjust the surface temperature. In doing this, the light path is divided into two paths: One passing through a silicon filter and measured by temperature sensor; The other directly measured by a silicon opto-electronic transistor. Here, the silicon opto-electronic transistor may cumulate signals within the range of the visible light and IR with wave length below 1.0 μm. A temperature sensor with a silicon filter, such as a thermister or a bolometer, may cumulate signals of IR with wave length above 1.0 μm.

When the surface temperature of the filament of the light source varies several tenths of one degree at the range of 3000 K, the variation in the reading of the two photosensors will be about 0.1% and the variation of the emission spectrum at the surface of the filament is about 0.1%, within said 0.8 to 1.7 μm range. Such variation may be controlled within the range of about, for example, 0.01% with a digital controller so that the aging of the filament may not be a problem. Of course, other means may be applicable to this invention, if similar effects are provided.

The photosensor 409 may be any photosensor which senses at least light waves within the scope of 0.8–1.7 μm. Applicable examples include diodes made of InGaAs, germanium, bolometer etc. Since photosensors do not generate heat, the aging of the photosensor will not be a problem in the measurement. A photosensor may be used for a long time once the method of adjustment is decided.

The light filter 408 comprises two Fabry-Perot interferometers. The driving forces of the interferometers comprises an electrostatic force and an elastic force. Here, silicon is selected to provide the elastic power due to the fact that no hysteresis would be found in the silicon material. In the embodiment of this invention, the elastic power is provided by a silicon corrugated diaphragm. This elastic structure helps to avoid the fatigue inherited in other elastic materials. As a result, the difference of the aging speed of the elements throughout the light path shall not be a problem to be dealt with, so far as the applicable range of wave lengths is concerned.

The affections to the optical signals caused by the heartbeats shall be obviated. In this invention, it is recommended that samplings are not conducted at the peak of the heartbeats. In addition to this, the signals of the heartbeats may be obtained by introducing a light beam, generated by a laser diode 404, into light path 405, 406 and 407 and to the sampling device 410, so to function as a reference of the sampling. Chopper 403 is used to increase the S/N ratio.

The analysis of the blood glucose content is conducted by the microprocessor 411. This microprocessor 411 is capable of learning. While information contained in the blood absorption spectrum include the content of glucose, vitamin C, uric acid etc., the lipidprotein content of a human body varies from one to another. The analysis of the blood content information is recommended to monitor the major contents in the blood. The microprocessor 411 is provided with a database for the general spectrum vectors of blood glucose contents. A database for the variation of the spectra of particular diabetics is also provided. These and other databases may be taken for reference in the analysis.

The volt signals obtained by the photodiode 409 is sampled by the sampling device 410 and analyzed by the microprocessor 411. The result as calibrated by the calibration device 412 may disclose the blood glucose content of the particular human body. The sampling device 410 and the calibration device 412 may be any applicable means or any commercialized product.

Figure 2:
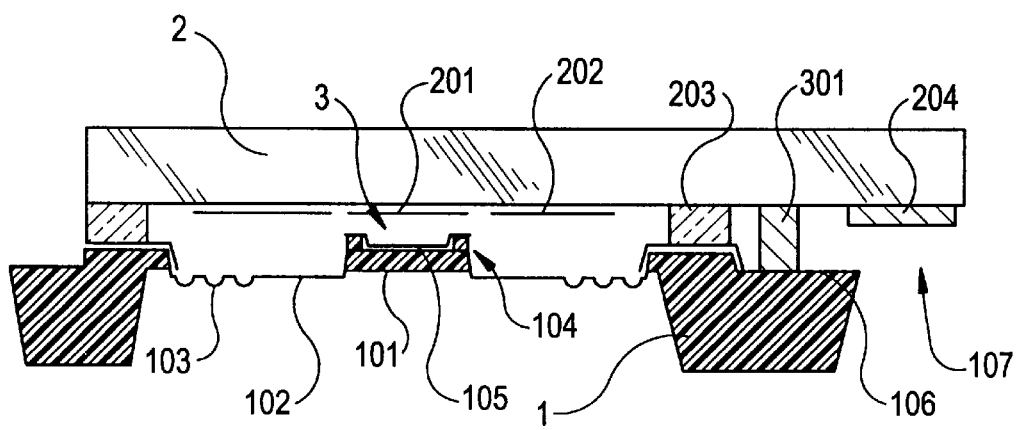
FIG. 2 illustrates the structure of a Fabry-Perot interferometer applicable in an embodiment of the non-invasive blood glucose meter of this invention.
Figure 3:
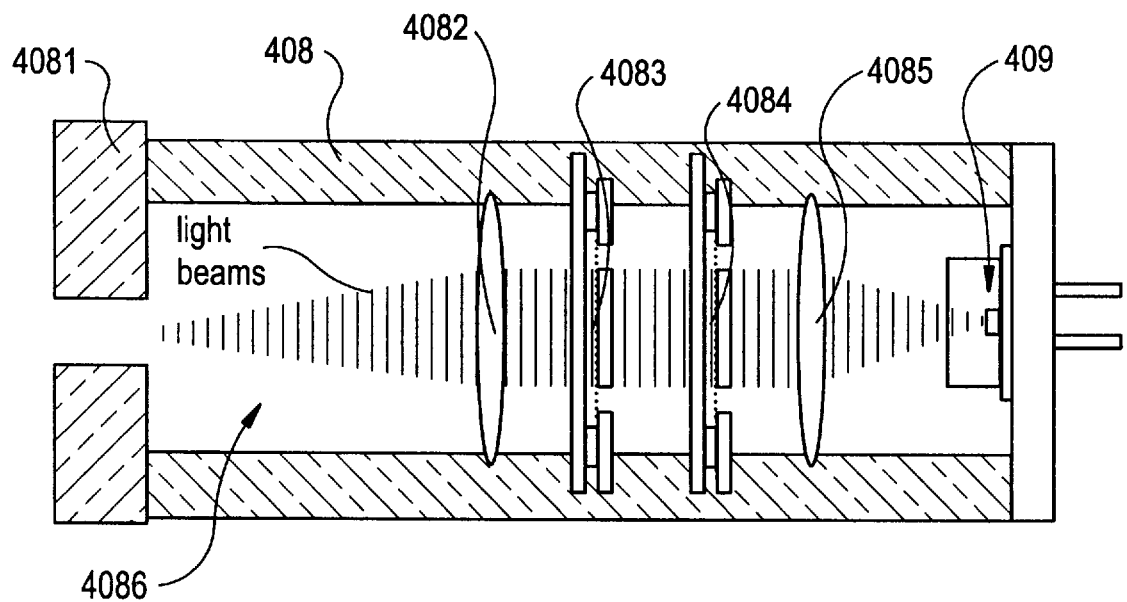
FIG. 3 illustrates the structure of the light filter of an embodiment of the non-invasive blood glucose meter of this invention.

The light filter 408 applicable in this invention comprises two Fabry-Perot interferometers 4083 and 4084. The two interferometers are concentrically in series, with their centers aligned to the axis of incident light to the photosensor 409, as shown in FIG. 3. FIG. 2 shows the structure of a Fabry-Perot interferometer. As shown in the figure, the Fabry-Perot interferometers 4083 and 4084 respectively comprise: a moveable silicon substrate 1, surrounded by corrugated diaphragm suspension, a fixed glass substrate 2, and an optical resonance cavity 3. Substrates 1 and 2 are bonded to form the optical resonance cavity 3. Microstructures may be formed on the silicon substrate 1. These microstructures include optical structures and mechanical structures. The glass substrate 2 is a fixed, transparent, volt-resistant and flat substrate. A spacer 203 and a connector 301 are positioned between the silicon substrate 1 and the glass substrate 2 such that the interference, the scanning and the filtering may be conducted in the interferometers 4083 and 4084. The connector 301 may be made of indium.

The driving powers of the Fabry-Perot interferometers 4083 and 4084 include an electrostatic power and an elastic power. The electrostatic power is used to drive the motion of the silicon substrate 1. By supplying a volt to the electrostatic power, the movable parts 101, 105 of the silicon substrate 1 may be driven by the static attraction and move towards the glass substrate 2, while the elastic power of the corrugated diaphragm 103 drives the movable parts 101, 105 to move departing from the glass substrate 2. By controlling the volt supplied to the electrostatic power, the distance between the silicon substrate 1 and the glass substrate 2 may be controlled. This means, movable parts 101, 105 and electode 202 organize an adjustable optical resonance cavity 3. The resonance cavity 3 provides high mechanical repeatability so that the quality of the spectra so measured may be used for further analysis.

Gold films 105 and 201 are supported by the glass substrate 2 and the silicon membrane 101. The supports 2 and 101 provide optical flatness. While glass substrate 2 and silicon membrane 101 are transparent to infrared with wave lengths from 0.8 to 1.7 μm, when the thickness of the silicon membrane 101 is well decided (for example, 5–8 μm), light with wave lengths within the applicable bands pass through the substrate 2 and the membrane 101. In other words, when the gap of the cavity equals to the times of the half wave length of the light within applicable bands, the light will pass through substrate 2 and membrane 101. This assembly may function as a filter where light with selected wave lengths may pass through. When two Fabry-Perot interferometers 4083 and 4084 are serially connected, a continuous spectrum may be obtained by scanning the wave lengths.

Because throughout the light path, from the incandescent light source 401 to the photosensor 409, all the components of the spectrum are processed with a single member and suited means to stabilize the surface temperature of the filament of the light source is used, the decay of any of the components may not contribute noises to the spectra and the quality of the spectra may be maintained.

The elastic power is supplied by the corrugated silicon membrane 103, positioned on the moveable silicon substrate 1. The advantage of the monolithic material is that no hysteresis will be found in the monolithic materials. A conductive surface 102 connected with an area diffused with highly concentrated boron (for example, $10^{20}$ atoms/cm$^3$) and a gold film with 20–35 nm thickness is formed on the substrate 1. This conductive surface 102 functions as a zero potential electrode and generates an electrostatic attraction force when functioning with the electrode 202 on the glass substrate 2. With the elastic force and the electrostatic force, plus the control of the volt supplied to the electrostatic power, the gap of the consonance cavity may be movably controlled. The relation between the gap of the resonance cavity and the volt supplied is monotonous and is repeatable.

The surface of the resonance cavity 3 is plated with a gold membrane and provides reflection index greater than 9%. A silicon membrane 105 is used to support the surface of the resonance cavity 3. The support 105 has high optical flatness at its surface. While the thickness of the support 105 is 5–8 μm, it is transparent to infrared with wave length from 0.8 to 1.7 μm. Such structure may function as a filter for the incident light. In order to maintain the distance between the coated surface 101 of the moveable substrate 1 and the coated surface 201 of the fixed substrate 2 so to avoid collisions between the membranes and delay in reactions, it is recommended to plant stoppers 104, 104 with 3 μm in height, such that the silicon substrate 101 would not move towards the glass substrate 2 at approximately 3 μm from the glass 201.

Wire pad 204 is provided on the glass substrate 2 so that the latter may electrically connected with external. The silicon material above area 107 shall be provided with a tunnel so that wires may be filled. The silicon membrane electrode is under the corrugated area 103 and the planar area 102 for approximately 5–8 μm in depth. After diffused with high concentrated baron, the opposite side is etched with KOH and an etching stop area is formed. A through hole may be formed by over-etching the dice so that wires may be positioned therein.

When the moveable silicon substrate 1 is driven by the electrostatic force, the corrugated diaphragm 103 can be easily deflected in compliance with the force, while the optically coated membrane 101 (with thickness of about 6–10 μm) on the moveable substrate 1 is able to avoid significant bending due to its sufficient rigidity, wherein the bending rigidity is proportional to the cubic power of the thickness of the membrane 101. In this invention, the bending rigidity of the coated membrane 101 is recommended to be at least 150 times larger than that of the corrugated structure 103. Hence, sufficient flatness on the surface of the moveable substrate 1 can be achieved and high resolution in the interference of the FPI may be obtained.

Because the material of substrate 2 is glass, it performs flat, solid, transparent and volt resistant characteristics and may be solder welded with indium. The optical flatness of the glass substrate supports the gold film 201 and is an important condition of the resonance cavity.

Chromium or aluminum may be plated onto the glass substrate to function as electrode 202 and to function as shelters to the incident light. The thickness of the electrode 202 may be about 2 μm.

The gap of the resonance cavity of the light filter 408 shall be maintained so that the gap varies within the range of, for example 100 nm. Spacer 203 may be used to provide such function. Material for the spacer 203 may be polyimide, spin-on-glass or thick photoresist.

The control volt introduced from external is supplied to electrodes 102 and 103 through the inter-substrate metal 301.

The optical interference cavity 3 is formed by bonding the silicon substrate 1 to the glass substrate 2. In preparing the interference cavity 3, the preform of the inter-substrate metal connector 301, such as an indium spindle, is positioned at the inter-substrate connector area of the silicon substrate 1, with an applicable depth of, for example, 5–8 μm. The thickness of the indium spindle shall be about several μm higher than that of the spacer 203. The glass substrate 2 is aligned with and covered onto the silicon substrate 1. Heat is applied to the assembly. After cooling down, the wafer is cut and a Fabry-Perot interferometer is obtained. If two Fabry-Perot interferometer are piled up to function as a continuous spectrum filter, the centers of the two Fabry-Perot interferometers shall be aligned with the incident light axis of photosensor 409.

In the light filter 408 only a single resonance is allowed to take place. Rough surface is thus provided on the external surface 101 of the silicon substrate 1. According to this invention, when the roughness is greater than 200 nm, no undesired interference will take place at both sides of the silicon membrane. The rough surface may be prepared with any conventional art.

FIG. 3 shows a light filter comprising two Fabry-Perot interferometers. According to this figure, the incident light passes entrance 4081, space 4086 and adjusted by lens 4082 to form parallel light beams which then pass the two Fabry-Perot interferometers 4083 and 4084 and sensed by photosensor 409. To ensure the parallelism of the incident light beams, the non-parallel light components of the incident light is filtered out by the long space 4086.

Light measured by photosensor 409 is decayed by the silicon membranes and filtered by the two Fabry-Perot interferometer. The photosensitive coefficient spectrum of the photosensor 409 may be converted into volt signals. The signals are modified by sampling device 410 and input to microprocessor 411. A continuous spectrum may be obtained by scanning the applicable bands with combinations of different widths of the interference cavity.

In order to enhance the correctness of the information, a laser diode or an LED 404 is used to calibrate the basis of the spectrum. The calibrator 412 may reduce the influence of the noises coming from the system itself.

EMBODIMENTS

Figure 4:
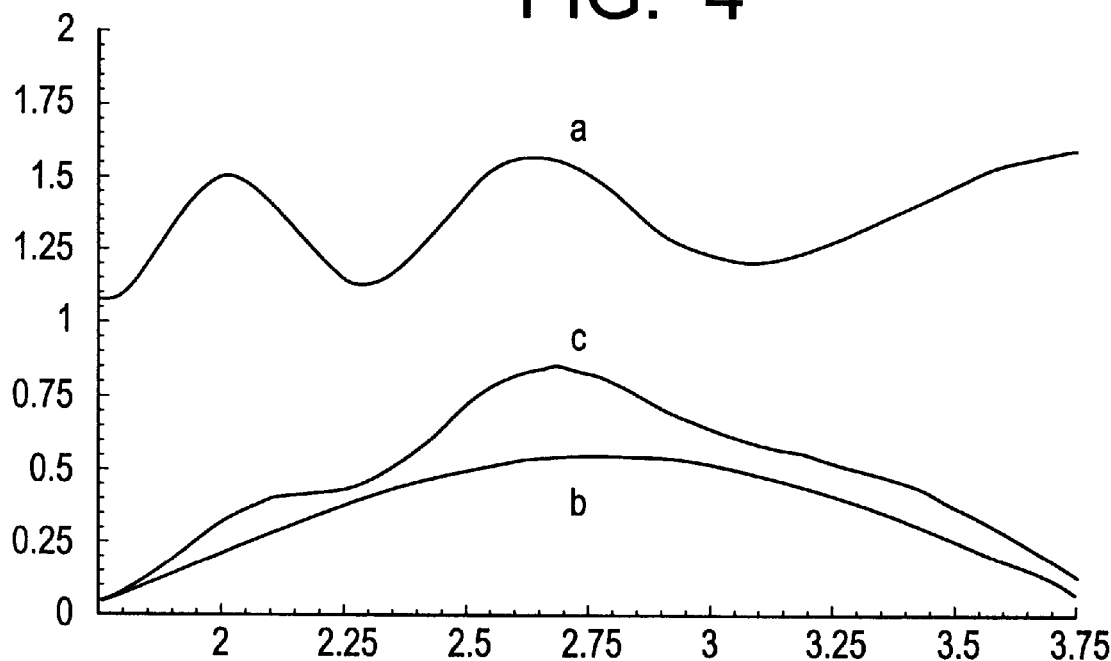
FIG. 4 shows the spectrum of the incident light (curve a), the spectrum of the multiplication of the sensitivity of InGaAs photo diode and the compound transmittance of FPIs (curve b) and the spectrum of the multiplication of curve a and curve b (curve c).
Figure 5:
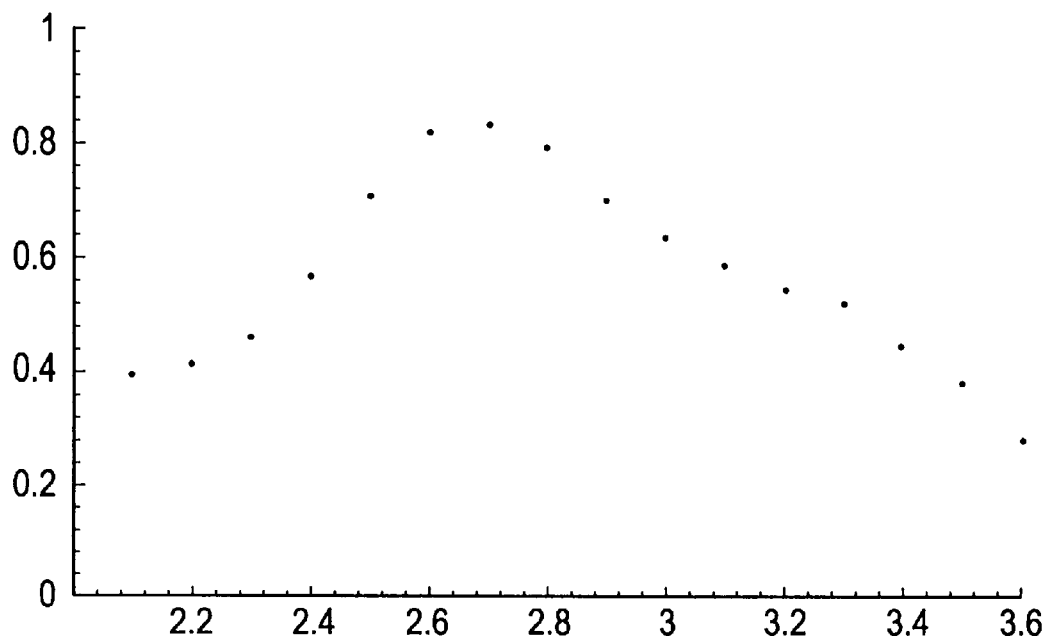
FIG. 5 illustrates the simulated near-IR absorption spectrum of blood, as measured by the non-invasive blood glucose meter of this invention.

Simulation is conducted under Mathamatica 3.0 (a software provided by Wolfram Research). FIG. 4 shows the spectrum of the incident light (curve a), the spectrum of the multiplication of the sensitivity of InGaAs photo diode and the transparency of silicon membranes (curve b) and the spectrum of the multiplication of curve a and curve b (curve c). In FIG. 4, curve a is an hypothetical incident spectrum. Since a linear axis is needed to integrate the spectral transmittance of the incident light, the x-axis represents the frequency under the unit of $10^{14}$ Hz. The multiplication of the sensitivity of the InGaAs photosensor and the light transparency of silicon is represented by curve b and the multiplication of curves a and b is curve c. Suppose the ranges of variations in the gap of the resonance cavity are 6.2–3.2 $\mu$m and 15–14 $\mu$m respectively and the transparency spectrum of a single interferometer is comb-like. If the gap of interferometer 4084 is set to 15 $\mu$m, when the gap of interferometer 4083 varies, a corresponding transparency spectrum may be read at each step of variation. When the combination transparency integration (ptwo) of the two resonance cavities is obtained, 16 sets of linear equations (when 16 variables are used), are resolved and the results are shown in FIG. 5. FIG. 5 illustrates the near-IR absorption spectrum of blood, as simulated under the non-invasive blood glucose meter of this invention. As shown in this figure, the 16 points comply with the spectrum of the combination of the sensitivity of InGaAs photo diode and the transparency of silicon membranes (curve b of FIG. 4).

The equations are given as follows:

$$a_{ij}P_j = P_{sj}(i,j=1,2,3,\ldots 16) \quad (1)$$

wherein $a_{ij}$ is the compound transparency which is the integration of the transparency of the two interferometers;

$P_j$: is the multiplication of the 16 incident spectra and the sensitivity of InGaAs and the transparency of Si.

$P_{sj}$: is a set of the signal currents of the photosensor at the 16 specific wavelengths.

The gap of interferometer 4084 is varied a step for, e.g. 0.2 $\mu$m, the incident is scanned again and a new set of spectrum spots are obtained. The above process is repeated and a virtually continuous spectrum is obtained.

In fact during the scanning of the resonance cavity, the variation curve of the signals currents of the photosensors varies within a great range. This illustrates that much more information is contained in the incident light. Even if the gap of one interferometer is kept unchanged, more information may be obtained from the signals by adjusting the gap of the other, although the matrix may be more complicated.

EFFECTS OF THE INVENTION

Since the absorption spectrum is obtained from a single light source and sensed by same photosensors, the quality of the information so obtained will be higher than in the conventional art, since in the conventional art, discrete infrared LED/PD's are used. Under the measurement of this invention, the noises coming from the measuring instrument itself may be reduced and the credibility of the spectrum may be increased.

As the present invention has been shown and described with reference to a preferred embodiment thereof, those skilled in the art will recognize that the above and other changes may be made therein without departing from the spirit and scope of the invention.

What is claimed is:

1. A non-invasive blood glucose meter comprising:

a light source for emitting light onto a human or animal tissue;

a light filter comprising at least two Fabry-Perot interferometers, for receiving light emitted from said light source after passing through said tissue to filter out noise contained in said light;

a light sensor for receiving light filtered by said filter and for transforming said filtered light into an electric format; and an analyzer for analyzing tissue information contained in said light transformed into said electric format, wherein:

each of said at least two Fabry-Perot interferometers comprises a resonance cavity gap adjustment means for adjusting the gap of a resonance cavity formed inside said at least two Fabry-Perot interferometers respectively and said filter filters said light according to the relation of a matrix of the compound transmittance of said at least two Fabry-Perot interferometers and the electric character of said light sensor, each of said at least two Fabry-Perot interferometers comprises a moveable silicon substrate, a fixed glass substrate and a resonance cavity formed by said substrates, said resonance cavity gap adjustment means adjusts said gap of said resonance cavity by supplying to said moveable silicon substrate an elastic force generated by a corrugated structure formed on said silicon substrate and an electrostatic force generated by a controlled electric voltage, and said moveable silicon substrate comprises an area diffused with highly concentrated boron and a gold film, both functioning as a zero potential electrode and said fixed glass substrate comprises another electrode and said two electrodes function to provide an electrostatic force.

2. The non-invasive blood glucose meter according to claim 1 wherein the wavelength of said light emitted by said light source is within the range of 0.8–1.7 $\mu$m.

3. The non-invasive blood glucose meter according to claim 1 wherein said light sensor senses light with wavelength within the range of 0.8–1.7 $\mu$m.

4. The non-invasive blood glucose meter according to claim 1 wherein the material of said light sensor is selected from the group consisting of InGaAs and Germanium.

5. The non-invasive blood glucose meter according to claim 1 wherein the surface of said resonance cavities is coated with a flat gold film with thickness of about 20–35 nm.

6. The non-invasive blood glucose meter according to claim 1 wherein the concentration of boron in said moveable silicon substrate is higher than $10^{19}$ atoms/cm$^3$.

7. The non-invasive blood glucose meter according to claim 1 wherein the thickness of said silicon substrate is within the range of 5–8 μm whereby infrared light with a wavelength within the range of 0.8–1.7 μm may pass through.

8. The non-invasive blood glucose meter according to claim 1, further comprising a semiconductor laser diode or a light emitting diode to supply calibration light source.

9. The non-invasive blood glucose meter according to claim 1, further comprising a chopper to chop said light into pulses before said light reaches said tissue.

10. The non-invasive blood glucose meter according to claim 1, further comprising a rigid silicon membrane with thickness of about 5–8 μm and a flexible corrugated membrane with thickness of about 1–3 μm.

* * * * *